United States Patent [19]

Kawakami et al.

[11] Patent Number: 5,366,867

[45] Date of Patent: Nov. 22, 1994

[54] METHOD OF DETERMINING VIABLE MICROBIAL CELL COUNT

[75] Inventors: Masaya Kawakami, Sagamihara; Susumu Seto; Seiken Tei, both of Yokohama, all of Japan

[73] Assignee: Nihon Millipore Kogyo, Yonezawa, Japan

[21] Appl. No.: 40,331

[22] Filed: Mar. 30, 1993

[30] Foreign Application Priority Data

Apr. 1, 1992 [JP] Japan ................................. 4-105299
Jan. 20, 1993 [JP] Japan ................................. 5-023420

[51] Int. Cl.$^5$ ......................... C12Q 1/66; G01N 21/76
[52] U.S. Cl. ........................................... 435/8; 435/4; 435/29; 435/39; 435/291; 435/968; 436/164; 436/172; 436/805
[58] Field of Search ................... 435/8, 4, 29, 39, 291, 435/968; 436/164, 172, 805; 358/83, 167, 184, 901

[56] References Cited

FOREIGN PATENT DOCUMENTS 3-40615 2/1991 Japan .
92-00145 2/1992 WIPO .

OTHER PUBLICATIONS

Tsai et al, *Biological Abstracts*, vol. 82, No. 12, Ref. #115437, 1986 (Proc Soc Exp Biol Med 183(1): 74–80, 1986).
Seto et al, *Chemical Abstracts*, vol. 118, p. 491, Ref. #208986p, 1993 (JP 05 30 997, 9 Feb. 1993).
Webster et al, *Biological Abstracts*, vol. 87, No. 6, Ref. #58283, 1988 (J Food Prot 51(12): 949–954, 1988).
Little et al, *Biological Abstracts*, vol. 81, No. 10 Ref. #91459, 1986 (J Food Prot 49(1): 18–22, 1986).
Kolbeck et al, *Journal of Clinical Microbiology*, vol. 21, No. 4, pp. 527–530, Apr. 1985.
Mafu et al, *Applied and Environmental Microbiology*, vol. 57, No. 6, pp. 1640–1643, Jun. 1991.
Tuncan et al, Applied and Environmental Microbiology, vol. 53, No. 1, pp. 88–91, Jan. 1987.
Selan et al, Journal of Clinical Microbiology, vol. 30, No. 7, pp. 1739–1742, Jul. 1992.
Brovko et al, *Biological Abstracts*, vol. 92, No. 6, Ref. #65854, 1991.
Schram et al, *Chemical Abstracts*, vol. 117, pp. 649–650, Ref. #88859e, 1992 (Biolumin. Chemilumin. Proc. Int. Symp. 6th, 1990 (Pub. 1991), 503–506).

*Primary Examiner*—Michael G. Wityshyn
*Assistant Examiner*—Abdel A. Mohamed
*Attorney, Agent, or Firm*—Andrew T. Karnakis; Huw R. Jones

[57] ABSTRACT

An improved method for determining a viable microbial cell count in a sample wherein the method comprises the steps of filtering a microbe-containing sample solution through a hydrophilic membrane, thereby trapping viable microbes thereon, then spraying an extracting reagent onto the viable microbes trapped on the membrane, thereby lysing the microbial cells. The lysed cells are then sprayed with a solution of luciferin-luciferase reagent, thereby inducing a luminesent signal. The signal is then quantified using a CCD-based device. The improvement comprises the use of a volatile alcohol extracting reagent for lysing the viable microbes, then evaporating the alcohol prior to spraying the luciferin-luciferase solution, leaving a concentrated ATP,containing solution for enhanced luminescent detection.

7 Claims, 1 Drawing Sheet

METHOD OF DETERMINING VIABLE MICROBIAL CELL COUNT

FIELD OF THE INVENTION

The present invention relates to a method of determining a viable count. More pariculatly, the invention relates to a rapid, convenient, and highly sensitive method of determining a viable count by detecting adenosine triphosphate (ATP) contained in microbes, which probably exist in industrial water, raw materials, intermediates, and products used in the industries of foods, pharmacy, cosmetics, electronics, etc.

DESCRIPTION OF THE PRIOR ART

In the industries of food, pharmacy, and cosmetics, etc., it is well-known that controlling viable microbes in industrial water, raw materials, intermediates, and final products is of extreme importance. Quality control of industrial water is also a matter of utmost concern in the electronics industry, and the number of viable microbes in the water must be monitored at any time. Consequently, determination of the viable count is an essential requirement in these industries.

In order to determine a viable count, a conventional, so-called "standard agar plate method" is generally employed, wherein viable microbes in a sample are cultured on an agar plate medium to form colonies for their detection. This process, however, is rather troublesome and, moreover, requires as long a time period as 24-72 hours for judgment. Thus, there has been a need in these industries to develop a more rapid and convenient process.

In an attempt to meet this need, a variety of methods for rapid detection have been proposed, including a bioluminescence method, wherein microbes are entrapped on a filter by filtering therethrough to measure the amount of adenosine triphosphate (ATP) in microbial bodies using a luminometer, thereby to calculate the viable count (Japanese Patent Laid Open No. 02-163098). When this method is applied to a sample solution with lower value of viable count, microbes are collected and densified on a filter, before determining the count using a luminometer (Japanese Patent Laid Open No. 02-57197). These methods, however, suffer from a problem in that the measuring vessel must contain viable microbes in a number above the lower limit of detection for the luminometer (for example, $\geq 1\times 10^3$ or $1\times 10^4$ cell/ml), thus requiring, particularly for a sample solution having extremely low viable count, a large volume of sample to be filtered.

Accordingly, the present inventors have previously developed a filter comprising a number of small hydrophilic filtration membrane sections substantially completely isolated from each other with hydrophobic partitions, and have invented a method comprising adding reagents for extraction and luminescence induction to the microbes collected on said filtration membranes by spraying, and treating the obtained preparation with a high-sensitivity bioluminescent image analysis system, the present inventors have filed a patent application (Japanese Patent Application No. 3-40615; and PCT-JP92-00145) covering this invention.

In this method, however, there exists a disadvantage, that is, the use of a conventional extracting reagent, containing a surfactant as its main constituent, during the process of extracting ATP from viable microbes entrapped on the filtration membrane causes concomitant extraction of ATP degradation enzymes by destruction of the cell membrane, resulting in degradation of extracted ATP, and tends to allow the extracted constituents to diffuse in the vicinity of the microbes, due to their high affinity to the membrane. This tendency has made the extraction of ATP with high concentration being retained difficult.

Alternatively, the use of such strong extracting reagents as trichloroacetic acid and perchloric acid gives rise to another problem that these reagents are left on the filtration membrane thereby making it highly acidic, resulting in inhibition of subsequent enzymatic reactions, thus requiring the addition of a sufficient amount of buffers to neutralize after extraction. This leaves the method still disadvantageous in that increased volume of reagents to be used causes dilution, diffusion, and flooding out, resulting in a decrease in the detection accuracy for ATP, and in somewhat indistinct outlines of bright spots in the vicinity of entrapped microbes.

SUMMARY OF THE INVENTION

It is an object of the present invention to provide an improved method of determining a viable count to solve the above mentioned problems during the process of extracting ATP in the known methods by means of detecting viable microbial ATP, in which method ATP can efficiently be extracted. ATP extracting reagents of excellent quality to clearly outline the bright spots upon the induction of luminescence, thereby resulting in an improvement in the manner of extracting ATP being achieved, The method also incorporates a bioluminescent with image analysis system.

As a result of intensive examination to solve the above problems into various extracting reagents conventinally used in the field of biochemistry to separate particular constituents, the present inventors have found the following facts and come to the present invention: a volatile extracting reagent having boiling point below 120° C. exerts a good effect to extract ATP from viable microbes, and successful results can be obtained when said extracting reagent is evaporated off under heating.

Accordingly, the present invention provides a method of determining a viable count in a sample characterized in that it comprises:
    filtering a solution of said sample through a hydrophilic membrane filter to entrap viable microbes contained therein on the filtration membrane of said filter;
    spraying a volatile extracting reagent having boiling point below 120° C. over said membrane to extract microbial ATP;
    thereafter or at the same time, subjecting said membrane to ambient or raised temperature to evaporate liquid constituents off;
    spraying a luminescence-inducing reagent of luciferin/luciferase type over said membrane to induce luminescence; and
    measuring the quantity of said luminescence using a suitable device for such measurement.

BRIEF DESCRIPTION OF DRAWINGS

In the following, further description will be made in more detail, referring to drawings wherein.

DETAILED DESCRIPTION OF THE INVENTION

Figure 1A:
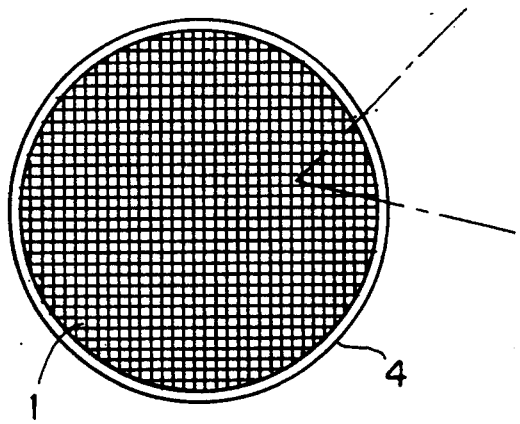
FIG. 1 (A)is a plan view of a membrane filter used in the method according to the present invention, and (B) an enlarged partial view thereof.
Figure 1B:
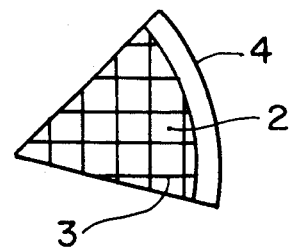
Figure 2:
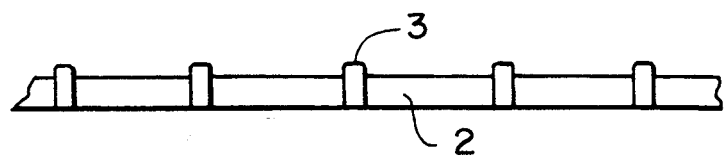
FIG. 2 is a sectional partial view of said membrane filter.

Referring to FIG. 1 and 2, a filter 1 used in performing the method according to the present invention comprises a number of small hydrophilic filtration membrane sections 2 substantially completely isolated from each other with hydrophobic partitions 3. This filter is made from a filter membrane 4 and hydrophobic partitions 3 by printing of a hydrophobic ink pattern on the membrane. The ink may penetrate into the filter element and the partitions may be flush with or higher than the surface of the membrane.

The ATP extracting reagent suitable for use in the present invention includes alcohols, ethers, esters, and halogenized derivatives of methane, ethane, methylene or ethylene, as well as acetonitrile, triethylamine and others having boiling point below 120° C. Methanol and ethanol are particularly preferred.

Extracting effect is further enhanced by admixing 0.1 to 5% by weight of hydrochloric acid, organic acids having b.p. below 120° C., or basic compounds such as ammonium hydroxide, organic amines and others having b.p. below 110° C. with the above alcohols. Though hydrochloric acid and organic acids having a tendency of volatility significantly enhance the extracting effect, they reduce the activity of the luminescence-inducing enzyme, when left in the sample even in a trace amount, thus necessitating more complete evaporation, and sometimes further spray of a neutralizing reagent to offset the acidity. Ammonium hydroxide is, therefore, particularly preferable, because it has high volatility and does not inhibit the induction of luminescence.

These ATP extracting reagents may be evaporated off at a temperature between ambient temperature and 80° C., preferably between 40° C. and 70° C. The use of a fine spray of said extracting reagents with an ultrasonic type sprayer (such as manufactured by Matsushita Electric Industries Co., Ltd.) is convenient and effective to add an exact amount required.

The membrane filter to be used in the method according to the present invention is a film or sheet of a hydrophilic filtration membrane, precisely made of plastic materials, such as hydrophilic polytetrafluoro-ethylene, hydrophilic poly(vinylidene fluoride), hydrophilic polysulfone, hydrophilic polycarbonate, hydrophilic polyamide, hydrophilic polyethylene and hydrophilic polypropylene, and cellulosic material, such as acetylcellulose and nitrocellulose, and having a number of uniform micropores with pore size from 0.1 to 1 $\mu$m.

It is preferable to use such a membrane filter as described in Japanese Patent Application No. 3-40615 (PCT-JP92-00145), comprising a number of hydrophilic filter sections substantially completely isolated from each other with latticed or circular hydrophobic micropartitions (for the plan view thereof, see FIG. 1). As the membrane filter suitable for sample solutions having a viable count on the filtration membrane being more than 100 cells, there is used, in addition to the above mentioned one, a filter cup equipped with a filtration membrane with a pore size from 0.1 to 1 $\mu$m, preferably from 0.2 to 0.45 $\mu$m at the bottom of a cylinder (diameter: 10–40 mm $\phi$) made of plastic materials, as described in Japanese Patent Application No. 2-253093.

In the following, the procedures for entrapping and measuring viable microbes according to the present invention will be described in further detail.

First, a sample solution is filtered using a filtration device, which is a cup-shaped vessel to be filled with the solution, equipped with the above membrane filter to entrap viable microbes thereon. The membrane filter is then subjected to a fine spray with the aforementioned ATP extracting reagent for the time period from 5 seconds to around 5 minutes, using such a sprayer as of ultrasonic type manufactured by Matsushita Electr. Ind. Co., Ltd. to extract microbial ATP, at a temperature from ambient to 80° C., preferably from 40° C. to 70° C. Proper time period for spray may vary depending on the species of microbes to be tested and the sort of extracting reagent to be used.

Heating may be applied during and/or after spray, but in a preferred manner, the membrane filter is subjected to the fine spray at ambient temperature, and then heated to a temperature from ambient to 80° C., preferably from 40° to 70° C. to rapidly evaporate the residual extracting reagent off.

Subsequently, a luminescence-inducing reagent of luciferin/luciferase type is added over the membrane filter. In the case where a sufficient count (more than 100 cells/membrane) is expected to enable the use of a luminometer, the reagent may be added onto the filter cup with a pipette, or with a usual sprayer, to induce luminescence. Otherwise (less than 100 cells/membrane), since a more precise spray in small amounts is required, spraying will be carried out with an ultrasonic type sprayer and the like.

In order to carry out the method according to the present invention more effectively, an increased concentration of the luminescence-inducing reagent of luciferin/luciferase type is used when inducing luminescence by spraying it with a sprayer, or by adding it with a pipette (in the case where such a large count as above 100 cells/membrane is expected). The reason is that the increased concentration will cause an increased rate of luminescence reaction, resulting in an increased quantity of luminescence. This is a more effective way for samples with particularly low count (i.e., less than 100 cells/ membrane, particularly less than 50 cells/membrane), which should be determined with a bioluminescence image anylysis system.

Thus, the concentration of luminescence-inducing reagent to be used is preferably increased to a range from twice to ten times, particularly from three to six times as high as standard Concentration. As a result, the rate of luminescence is accelerated to enhance the level of luminescence of bright spots, at the same time accelerating the speed of detection.

The term "standard concentration" as used herein means the concentration as specified for regular use of conventional luminescence-inducing reagents (for example, a luciferin/luciferase type reagent Lucifer LU TM commercially available from Kikkoman Co., Ltd.)

More particularly, when such a luminescence-inducing reagent as manufactured by Kikkoman Co., Ltd. (Lucifer TM), which is normally used in a diluted form of 70 mg of the dry reagent diluted with 5 ml of water, is used in a concentration from about three to six times higher than said concentration for regular use, as stated above, the time for emission of light after the spray of the reagent can be reduced, and the quantity of luminescence can be increased almost directly in proportion to its concentration.

The membrane filter thus allowed to emit light can be subjected to counting, using a luminometer, such as Luminescence Reader BLR-201™ (an improved model), Aloka Corporation, or to imaging bright spots appearing on the filter, using any device for bioluminescence image analysis system, such as ARGUS-50/CL ™ (provided with a tapered fiber), Hamamatsu Photonics, Co., Ltd. to determine the viable count. The latter bioluminescence image analysis system of improved type can process considerably faint luminescence with high sensitivity, and enables rapid data processing and analysis, as compared with conventionally used similar instruments, so that an unusually excellent method of determining a viable count can be actualized, in cooperation with the effect of the filter and spray of reagents according to the present invention.

Figure 3A:
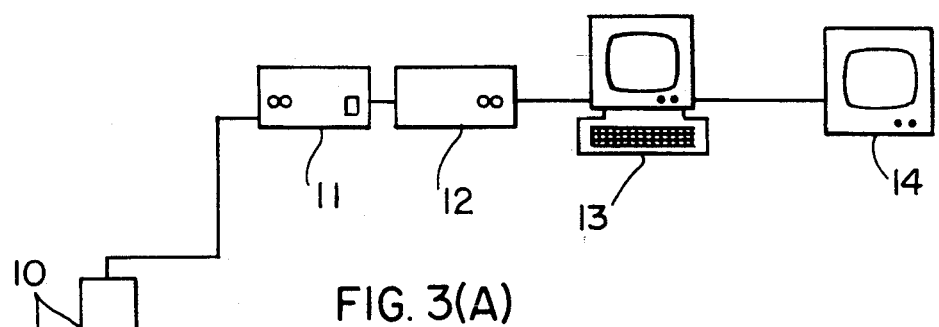
FIG. 3(A) is a schematic diagram of a bioluminescent image analysis system used in the method according to the present invention.
Figure 3B:
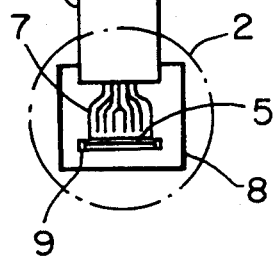
FIG. 3(B) is an enlarged partial view.
Figure 3B:
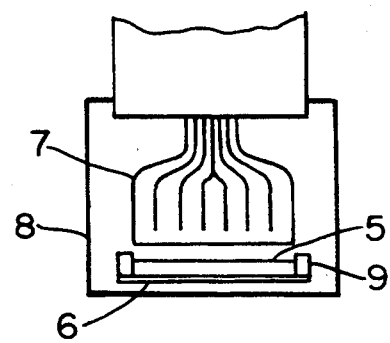

The outline of the system is as shown in FIG. 3, in which (A) is an entire outline and (B) is an enlarged partial view. This system comprises a preparation holder 9 for supporting the membrane filter (preparation) 5 after treatment with the aforementioned extracting and luminescence-inducing reagents; a total reflection plate 6; a shading housing 8; tapered fibers 7, which are juxtaposed to said membrane fileter as closely as possible to detect luminescence in a two-dimensional extent; an ultrahigh-sensitivity television camera 10 consisting of a photoamplifying component and a camera tube; a camera controller 11; an image processor 12; a data analysis device 13; and a monitor television 14. ARGUS-50/CL ™ of tapered fiber input type, Hamamatsu Photonics, Co., Ltd., or those having a similar counting performance is particularly preferred.

As the ultrahigh-sensitivity television camera, a cooled solid-state camera device (CCD) may be employed, wherein it is cooled to a temperature from about −30° C. to −120° C. to restrain noises from the camera itself so that it can accumulate even very faint light. For example, a cooled CCD digital imaging system is available from Hamamatsu Photonics. Alternatively, the system may be operated by placing the tapered fibers 7 in the camera tube portion and the ultrahigh-sensitivity television camera underneath the preparation holder and placing the preparation holder containing a preparation on the tapered fibers.

Desirably, preparation 5 is placed as closely as possible to tapered fibers 7, thereby to significantly enhance the measurement sensitivity. For the purpose of automatic counting, if desired, sprayer(s) for extracting and luminescence-inducing reagents, and other associated equipments such as preparation carrier may be set in a combined format.

To determine a viable count, preparation holder 9 bearing a preparation (a membrane filter retaining microbes to be tested) after the aforementioned luminescence-inducing process is kept in close contact with the surface of tapered fibers 7, while the luminescence emitted from microbial bodies is introduced through the ultrahigh-sensitivity television camera 10 and the camera controller 11 into the image processor 12, where photons are accumulated for the time period from 30 to 180 seconds, e.g., 120 seconds in a two-dimensional fashion to pick up the image, which is then processed by the data analysis device 13 to be displayed on the monitor television 14 with bright luminescence originated from viable microbes only remaining and faint noise luminescence being erased. Since this processing eliminates any luminescence originated from other than the microbial bodies, it gives substantial correspondence of the number of the bright spots counted to the viable count.

EFFECTS OF THE INVENTION

In the present invention, viable microbes are entrapped on a membrane filter in an advantageous form as hitherto stated, and subjected to the microbial ATP extraction in situ, using a fine spray of a preferred volatile extracting agent. Subsequently, this solvent is rapidly evaporated off by subjecting the filter to a temperature from ambient to 80° C., preferably from 40° C. to 70° C., before a direct spray of luminescence-inducing reagent to induce luminescence, which is subjected to a measurement using a high-sensitivity bioluminescence image analysis system to determine the viable count.

The use of a preferred extracting reagent and evaporation thereof thus eliminates such an existence of any residual constituents of the extracting reagent as seen in the case of using conventional extracting reagents based on an aqueous solution of surfactants. Substantial absence of residual extracting reagent eliminates the possibility of inhibtion of luminescence thereby. Also, since the activity of ATP degradation enzymes is inhibited, no attenuation of luminescence occurs. Further, there exists no diffusion of ATP in the vicinity of each microbe, making the localization thereof more distinct. As a result, the detection sensitivity of the system is considerably increased, and the time and labor for determination is significantly reduced.

If a membrane filter comprising a number of small hydrophilic sections completely isolated from each other with hydrophobic partitions is employed as the filter, all the viable microbes are well dispersed and entrapped within the small sections. Also, the extracting solution (solution of ATP extracting reagent) and the solution of luminescence-inducing reagent (luciferin/luciferase type) both to be sprayed thereon are designed so as to remain within the sections without diffusing outside from each section nor to be diluted. This allows the microbial constituent that has become light emitting to be retained closely at the location of the microbe in a relatively high concentration, so that the above mentioned effectiveness are further augmented, enabling an extremely sensitive determination to be attained.

Furthermore, if the preparation (membrane filter) thus allowed to emit light is used with a bioluminescence image analysis system, in which a highly-sensitive and selective detection of bright spots is available, any noise luminescence originated from other than viable microbes can readily be erased, so that even an extremely low viable count (e.g., several cells/membrane), can be determined automatically, as well as rapidly and conveniently.

EXAMPLES

The present invention will be further illustrated in the following description of the examples.

EXAMPLE 1

*Saccharomyces cerevisiae* (IFO 0209) was cultured in a glucose/peptone medium (Eiken Chemicals Co., Ltd.) for overnight. 5 ml of sample solution containing about 100 cells/ml, obtained by diluting the above culture with phosphate buffer (pH=7.5), was filtered to entrap the microbes, using a Millicell-CM ™ (Nippon Millipore Co.), a culture cup equipped with a biopore membrane (0.4 μm) at the bottom of a cylinder made of polystyrene, and a fine spray ( i.e. a spray of very fine mist) of 90% ethanol was applied to the Millicell-CM membrane for 30 seconds, using a sprayer of ultrasonic type from Matsushita Electr. Ind. Co., to extract ATP from the microbes.

After evaporating the solvent off at a temperature from 50° C. to 60° C., a luminescence-inducing reagent (Lucifer-LU TM, Kikkoman Co., Ltd.) was sprayed on the membrane for 20 seconds, to induce luminescence, and thereafter the quantity of luminescence was measured for one minute to calculate the viable count, using a luminometer (Luminescence Reader TM BLR-201, improved type, Aloka Corp.) with results obtained as shown in Table 1. For comparison, results of determination of the viable count obtained from the same sample solution by means of standard agar plate method using a potatoe dextrose/agar medium (Nissui Seiyaku Co., Ltd.) are also shown in Table 1.

TABLE 1

| Standard Agar Plate (CFU/5 ml sample soln.) | Present Invention (viable count/5 ml sample soln.) |
|---|---|
| 529 | 540 |
| 511 | 532 |
| 532 | 512 |
| 501 | 526 |
| 524 | 544 |

EXAMPLE 2

After *Escherichia coli* (IFO 13898) was cultured in m-TGE medium (DIFCO Laboratories) for overnight, followed by entrapping the microbes on a Millicell-CM TM as used in Example 1 by filtering therethrough, 5 ml of sample solution containing about $1 \times 10^3$ cells/ml, obtained by diluting the above culture with phosphate buffer (pH=7.5), the same procedure was carried out as in Example 1, except that the solvent was evaporated off by leaving the preparation at ambient temperature for three minutes, to calculate the viable count, with results obtained as shown in Table 2, along with the results obtained by means of standard agar plate method.

TABLE 2

| Standard Agar Plate (CFU/5 ml sample soln.) | Present Invention (viable count/5 ml sample soln.) |
|---|---|
| 5,130 | 5,020 |
| 5,210 | 5,342 |
| 5,152 | 5,244 |
| 5,228 | 5,310 |
| 5,301 | 5,190 |

EXAMPLE 3

Using Saccharomyces cerevisiae (IFO 0209), the same procedure was carried out as in Example 1, except that Millicell-GVWP TM (Nippon Millipore Co.) equipped with a hydrophilic PVDF membrane was used instead of Millicell-CM TM, and methanol was used instead of ethanol, to obtain results as shown in Table 3, along with results obtained by means of standard agar plate method.

TABLE 3

| Standar Agar Plate (CFU/5 ml sample soln.) | Present Invention (viable count/5 ml sample soln.) |
|---|---|
| 508 | 488 |
| 479 | 518 |
| 511 | 522 |
| 520 | 508 |
| 491 | 516 |

EXAMPLE 4

An overnight culture solution of Saccharomyces cerevisiae (IFO 0209) in a glucose/peptone medium was diluted with phosphate buffer (pH=7.5) to obtain a sample solution containing about 20 cells/ml. 1 ml of this solution was filtered through a uniquely latticed hydrophilic durapore filtration membrane (25 mm φ, Nippon Millipore Co.), and, after washing the membrane and collecting the microbes thereon, the filtration membrane was removed from the filter and dried.

A fine spray of 90% ethanol was then applied to the membrane for 30 seconds, as in Example 1, to extract ATP, and, after evaporating the solvent off at a temperature from 50° C. to 60° C., a fine spray of a luminescence-inducing reagent (Lucifer-LU TM, Kikkoman Co., Ltd.) was applied thereto for 10 seconds to induce luminescence.

The preparation was loaded to an image analyzer (ARGUS-50/CL TM, Hamamatsu Photonics Co., Ltd.), and, after accumulating photons for two minutes and processing the image, only bright spots having luminance above the threshold value were imaged to determine the viable count. The results obtained are shown in Table 4, along with the results from determining the viable count for the same sample solution by means of standard agar plate method using a potatoe dextrose/agar medium cultured at 30° C. for 48 hours,

TABLE 4

| Standard Agar Plate (CFU/1 ml sample soln.) | Present Invention (No. of bright spot/membrane) |
|---|---|
| 23 | 20 |
| 26 | 21 |
| 21 | 20 |
| 23 | 19 |
| 20 | 17 |

EXAMPLE 5

An overnight culture solution of *Staphylococcus aureus* (IFO 3060) in a nutrient broth (Eiken Chemicals Co., Ltd.) was diluted with phosphate buffer (pH=7.5) to obtain a sample solution containing about 30 cells/ml. 1 ml of this solution was filtered through a filtration membrane as used in Example 4, and, after collecting microbes, extracting ATP, and inducing luminescence, as in Example 4, only bright spots originated from viable microbes were imaged to determine the viable count, with results obtained as shown in Table 5. Also, the results obtained from the same sample solution with standard agar plate method using the nutrient broth cultured at 37° C. for 48 hours are shown in Table 5.

TABLE 5

| Standard Agar Plate (CFU/1 ml sample soln.) | Present Invention (No. of bright spot/membrane) |
|---|---|
| 36 | 33 |
| 32 | 30 |
| 35 | 30 |

TABLE 5-continued

| Standard Agar Plate (CFU/1 ml sample soln.) | Present Invention (No. of bright spot/membrane) |
| --- | --- |
| 30 | 27 |
| 32 | 27 |

EXAMPLE 6

A sample solution containing about 30 cells/ml of Saccharomyces cerevisiae (IFO 0209) was prepared by culturing and diluting according to Example 4. 1 ml of this solution was filtered through a filtration membrane as used in Example 4, and, after collecting microbes, a fine spray of methanol containing 3% by weight of triethylamine was applied to the membrane for 30 seconds, to extract ATP.

After leaving it at ambient temperature for three minutes, then inducing luminescence by spraying the luminescence-inducing reagent for 10 seconds, and evaporating solvent off at a temperature from 50° C. to 60° C., as in Example 4, the preparation was loaded to an image analyzer to accumulate photons for two minutes, and only bright spots having luminance above the threshold value and originated from viable microbes were imaged to determine the viable count. The results obtained are shown in Table 6. Also, the results obtained from the same sample solution by means of standard agar plate method using a pepton dextrose/agar medium cultured at 30° C. for 48 hours are shown in Table 6.

TABLE 6

| Standard Agar Plate (CFU/1 ml sample soln.) | Present Invention (No. of bright spot/membrane) |
| --- | --- |
| 29 | 26 |
| 33 | 28 |
| 35 | 30 |
| 33 | 31 |
| 30 | 28 |

EXAMPLE 7

A sample solution containing about $1 \times 10¢ 3$ cells/ml of *Staphylococcus aureus* (IFO 3060) was prepared by culturing and diluting as in Example 5. After filtering 5 ml of this solution and collecting microbes on the membrane as in Example 5, ATP was extracted as in Example 1, using 90% ethanol containing 1% of ammonium hydroxide (aqueous ammonia) instead of 90% ethanol, then luminescence was induced by spraying a luminescence-inducing reagent (Lumit-PM TM, Lumac Co.) for 20 seconds, and the quantity of luminescence was measured.

In this example, the entire procedure was repeated with replacing ATP extracting reagent only with another reagent (NRB TM, Lumac Co.) to compare the quantity of luminescence. The results obtained are shown in Table 7.

TABLE 7

| NRB (count/min.) | EtOH = NH$_4$OH (count/min) |
| --- | --- |
| 112 | 251 |
| 136 | 223 |
| 128 | 237 |
| Av. 125 (100%) | Av. 237 (190%) |

EXAMPLE 8

Each 0.5 μl of aqueous solution containing either $4 \times 10^{-13}$ g, $4 \times 10^{-14}$ g, or $2 \times 10^{-14}$ g of ATP was spotted on a uniquely latticed hydrophilic filtration membrane (47 mmφ, Nippon Millipore Limited) as used in Example 4, and dried.

A fine spray of luminescence-inducing reagent used usually in the present examples (Kikkoman Co., Ltd.) was applied to the membrane for 10 seconds separately in two concentrations, i.e., normal concentration and four times as dense concentration as normal one. Accumulation of photons for two minutes was carried out in the same manner throughout this experiment. The results obtained are shown in Table 8. Values represent the amount of photons emitted from an area of $25 \times 25$ pixels on the monitor.

TABLE 8

| conc. of ATP (g/0.5 μl) | conc. of reagent | |
| --- | --- | --- |
| | normal. | ×4 |
| $4 \times 10^{-13}$ | 16,200 | 22,360 |
| $4 \times 10^{-14}$ | 590 | 2,350 |
| $2 \times 10^{-14}$ | 30 | 390 |

EXAMPLE 9

A diluted solution of Saccharomyces cerevisiae (IFO 0209) containing about 100 cells/ml was prepared as in Example 1. 0.2 ml of this solution was filtered through a uniquely latticed hydrophilic filtration membrane (47 mmφ, Nippon Millipore Limited) and dried. Extracting reagent was then sprayed for 30 seconds as in Example 1 to extract ATP.

Thereafter, a fine spray of luminescence-inducing reagent used usually in the present examples was applied to the membrane for 10 seconds as in Example 8, i.e., in normal concentration and in four times as dense concentration as normal one. Accumulation of photons for two minutes was carried out in the same manner throughout this experiment. The results obtained are shown in Table 9.

TABLE 9

| concentration of luminescence-inducing reagent | | | |
| --- | --- | --- | --- |
| normal | | ×4 | |
| No. of bright spot/membrane | quantity of luminescence* | No. of bright spot/membrane | quantity of luminescence* |
| 15 | 45,133 | 16 | 1,456,113 |
| 13 | 44,721 | 12 | 1,411,232 |
| 11 | 43,414 | 13 | 1,395,311 |

*total amount of photons detected per membrane.

From the above results of Examples 1–9, as shown in Tables 1–9, it can be understood that similar values are obtained by means of the time-consuming standard agar plate method and the method according to the present invention, and that the latter method is well applicable to determining a viable count.

ADVANTAGES OF THE INVENTION

The present invention is advantageous in that it provides a method of determining a viable count using the techniques of the ATP bioluminescence method, wherein the use of particular volatile extracting reagents and an evaporating process allows ATP to be extracted effieciently from viable microbes entrapped and collected on a membrane filter, and prevents any inhibition of enzyme (i.e., luciferase) activity and adverse effect of ATP degeneration enzymes during subsequent luminescence-inducing process. As a result, a more sensitive and rapid method of determining a viable count, as compared with conventional methods, has been actualized.

The present invention is also advantageous in that, in the present method, the use of a membrane filter comprising small sections isolated from each other with slightly protruded partitions, and a spray process for adding reagents, combined with an improved bioluminescence image analysis system, which makes a highly sensitive and rapid detection of even faint luminescence possible, allows a viable count to be determined in a substantially reduced time, as compared with conventional methods, and further enables to carry out a highly sensitive, rapid, and convenient determination for samples having a relatively small count, determination of which has formerly been difficult.

We claim:

1. In a method for determining a viable microbial cell count in a sample wherein the method comprises the steps of filtering a microbe-containing sample solution through a hydrophilic membrane, thereby trapping viable microbes thereon; spraying an extracting reagent onto the viable microbes entrapped on said membrane thereby lysing microbial cells and extracting adenosine triphosphate (ATP); spraying a solution of luminescence-inducing luciferin-luciferase reagent onto said membrane thereby inducing luminescence; and measuring the quantity of luminescence; wherein the improvement comprises using a volatile alcohol as said extracting reagent to extract ATP; and evaporating said volatile alcohol extracting reagent prior to said spraying of said luciferin-luciferase reagent, thereby enhancing detection of extracted ATP.

2. The method for determining a viable microbial cell count according to claim 1, wherein said hydrophilic membrane comprises a number of small hydrophilic sections substantially isolated from each other with hydrophobic partitions.

3. The method for determining a viable microbial cell count according to claim 1, wherein said hydrophilic membrane is a plastic filter cup equipped with a hydrophilic filtration-membrane at the bottom of a cylinder.

4. The method for determining a viable microbial cell count according to claim 1, wherein said hydrophilic membrane is made of hydrophilic forms of material selected from the group consisting of polytetrafluoroethylene, poly(vinylidene fluoride), polycarbonate, polyamide, polysulfone, polyethylene, polypropylene, acetylcellulose and nitrocellulose.

5. The method for determining a viable microbial cell count according to claim 1, wherein said volatile alcohol extracting reagent for adenosine triphosphate is methanol or ethanol.

6. The method for determining a viable microbial cell count according to claim 1, wherein said volatile alcohol extracting reagent for adenosine triphosphate is a mixture of methanol or ethanol with 0.1 to 5% by weight of ammonium hydroxide.

7. The method for determining a viable microbial cell count according to claim 1, wherein said membrane is subjected to a temperature from 40° C. to 70° C. during the evaporation step.

* * * * *